United States Patent
Ghose et al.

(10) Patent No.: US 11,445,973 B2
(45) Date of Patent: Sep. 20, 2022

(54) SYSTEM AND METHOD FOR EARLY DETECTION OF MILD COGNITIVE IMPAIRMENT IN SUBJECTS

(71) Applicant: Tata Consultancy Services Limited, Mumbai (IN)

(72) Inventors: Avik Ghose, Kolkata (IN); Arijit Chowdhury, Kolkata (IN); Sonia Sharma, Guwahati (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1016 days.

(21) Appl. No.: 16/156,971

(22) Filed: Oct. 10, 2018

(65) Prior Publication Data

US 2019/0269360 A1 Sep. 5, 2019

(30) Foreign Application Priority Data

Mar. 1, 2018 (IN) .............................. 201821007810

(51) Int. Cl.
| | |
|---|---|
| *A61B 5/00* | (2006.01) |
| *G16H 50/20* | (2018.01) |
| *G16H 50/70* | (2018.01) |
| *G16H 10/60* | (2018.01) |
| *A61B 5/11* | (2006.01) |

(52) U.S. Cl.
CPC .......... *A61B 5/4088* (2013.01); *A61B 5/4064* (2013.01); *A61B 5/7232* (2013.01); *G16H 50/20* (2018.01); *G16H 50/70* (2018.01); *A61B 5/1118* (2013.01); *G16H 10/60* (2018.01)

(58) Field of Classification Search
CPC ... A61B 5/4088; A61B 5/7264; A61B 5/7275; A61B 5/4064; A61B 5/7232; A61B 5/1118; G16H 50/20; G16H 50/70; G16H 10/60
See application file for complete search history.

(56) References Cited

PUBLICATIONS

Che, C. et al. "An RNN Architecture with Dynamic Temporal Matching for Personalized Predictions of Parkinson's Disease," *Proceedings of the 2017 SIAM International Conference on Data Mining*, Houston, TX, Apr. 27-29, 2017; 9 pages.

(Continued)

*Primary Examiner* — Scott M. Getzow
(74) *Attorney, Agent, or Firm* — Finnegan, Henderson, Farabow, Garrett & Dunner, LLP (57) ABSTRACT

This disclosure relates generally to detection of mild cognitive impairments in subjects. The method and system proposed provides a continuous/seamless monitoring platform for MCI detection in subjects by continuously monitoring routine activities of subjects (Activities of Daily Living (ADL)) in a smart environment using plurality of passive, unobtrusive, binary, unobtrusive non-intrusive sensors embedded in living infrastructure. The proposed method and system detects symptoms of MCI at the onset of the disease, while also addressing issue of sensor failures that causes gaps in the data. The collected sensor data is pre-processed in several stages which includes which includes pre-processing of sensor data, behavior deviation detection, and abnormality detection and so on. Further, the disclosure also proposes an autoencoder based technique, to reduce the dimension of the data to find personalized deviations in behavior of a subject which is used to detect if a subject could be a potential case of MCI.

15 Claims, 6 Drawing Sheets

(56) References Cited

PUBLICATIONS

Wang, W. "Generalized Autoencoder: A Neural Network Framework for Dimensionality Reduction," *2014 IEEE Conference on Computer Vision and Pattern Recognition Workshops*, Columbus, OH, Jun. 23-28, 2018; pp. 490-497.

Lipton, Z.C. et al. "Learning to diagnose with LSTM recurrent neural networks," *ICLR 2016*, San Juan, Puerto Rico, May 2-4, 2016; pp. 1-18.

Nourhashemi, F. et al. (Nov. 2005). "Living alone with Alzheimer's disease: Cross-sectional and longitudinal analysis in the real.fr study," *The Journal of Nutrition, Health & Aging*, vol. 9, No. 2; pp. 117-120.

SYSTEM AND METHOD FOR EARLY DETECTION OF MILD COGNITIVE IMPAIRMENT IN SUBJECTS

CROSS-REFERENCE TO RELATED APPLICATIONS AND PRIORITY

The present application claims priority from Indian provisional specification no. 201821007810 filed on 1Mar., 2018, the complete disclosure of which, in its entirety is herein incorporated by references.

TECHNICAL FIELD

The disclosure herein generally relates to field of neurological disorder detection and, more particularly, to a system and a method for detection of Mild Cognitive Impairment (MCI) in subjects.

BACKGROUND

Neurological disorders are diseases of brain, spine and nerves that connect brain and spine. Neurological disorders include diseases such as Alzheimer's, dementia and so on. Early detection and diagnosis of symptoms of the neurological disorders may aid in halting the progress of the disease. Common symptoms for neurological disorders include partial or complete paralysis, muscle weakness, MCI among many others with respect to functioning of neurological system.

Mild Cognitive Impairment (MCI) is a commonly found symptom for neurological disorders among subject/geriatric subjects/elders. MCI causes a slight but noticeable and measurable decline in cognitive abilities of subject. Thus by constantly monitoring routine activities of a subject over a period of time, progression of MCI can be detected. The routine activities of a subject can be monitored in several ways such as by providing Ambient Assisted Living (AAL) among several other existing methods. AAL utilizes several sensors to monitor routine Activities of Daily living (ADL) of subjects who use them. During the monitoring process, in case of detection of deviation in routine activities over a period of time, progression of MCI is detected.

The existing methods monitoring routine activities of subject use cameras or sensors for collecting data, however usage of cameras or sensors invades privacy, while sensors are circuitry devices and may be prone to failure due to technical issues such as power outage or may even sound a false alarm. Further certain existing methods use plurality of advanced non-intrusive sensor technologies such as infrastructure based sensors to monitor ADLs. However the sensor data collected using advanced non-intrusive sensors is high dimensional. Further, the high dimensional data collected by non-intrusive sensors cannot be processed by existing machine learning due to its enormous quantity.

SUMMARY

Embodiments of the present disclosure present technological improvements as solutions to one or more of the above-mentioned technical problems recognized by the inventors in conventional systems. For example, in one embodiment, a method for a continuous/seamless monitoring platform detection of Mild Cognitive Impairment (MCI) is provided. The routine activities of subjects, housed in a smart environment is continuous monitored by plurality of non-intrusive sensors embedded in living infrastructure. Further the collected sensor data is processed in several stages, which includes pre-processing of sensor data, behavior deviation detection, abnormality detection and so on to detect if a could be a potential case of MCI illness.

In another aspect, a method for detection of Mild Cognitive Impairment (MCI) in a subject is provided. The method includes receiving sensor data from a plurality of sensors, wherein the received sensor data indicates Activities of Daily Living (ADL) pertaining to a subject for a specific time interval. Further corrupt sensor data in the received sensor data is substituted, by using Long Short-Term Memory (LSTM), with correct sensor data to generate corrected sensor data, wherein the corrupt sensor data is substituted with the correct sensor data based on a learning pattern and historical data stored in a database. Further, a semantic vector representation of the corrected sensor data is generated, wherein the semantic vector representation comprises a plurality of sub-vectors, wherein each of the plurality of sub-vectors comprise of a subset of the corrected sensor data of a pre-determined time interval. Furthermore, size of the semantic vector representation of the corrected sensor data is optimized, by using an auto encoder to generate an optimized vector data. Then, a dynamic threshold parameter ($\emptyset$) is estimated based on one or more similarity values obtained from a comparison of (i) the optimized vector data for the time interval with (ii) an adjacent optimized vector data comprising corresponding corrected sensor data stored in the database. Furthermore, size of the semantic vector representation of the corrected sensor data is optimized, by using an auto encoder to generate an optimized vector data. Further during optimizing using an auto encoder, size of the semantic vector representation of the corrected sensor data to generate an optimized vector data comprises: applying a dimension reduction based window sizing technique on the semantic vector representation of the corrected sensor data. Then, a dynamic threshold parameter ($\emptyset$) is estimated based on one or more similarity values obtained from a comparison of (i) the optimized vector data for the time interval with (ii) an adjacent optimized vector data comprising corresponding corrected sensor data stored in the database. Further, a comparison is performed for one or more similarities values with the dynamic threshold parameter; upon detecting behavior deviation of the user, analyzing the semantic vector representation corresponding to the optimized vector data and performing a comparison of the analyzed semantic vector representation with a previous adjacent semantic vector representation; and storing a start time and an end time specific to the behavior deviation of the user in a database. Further one or more corresponding sub-vectors is analyzed based on the start time and the end time specific to the behavior deviation of the user; and tagging the analyzed one or more corresponding sub-vectors as one or more abnormal vectors. Finally one or more abnormalities indicative of behavior deviation of the subject is detected based on the comparison, wherein one or more random activities between the start time and the end time is compared and a flag indicative of an abnormal behavior is generated when duration of the one or more repeated random activities is less than or greater than an actual duration of a corresponding particular activity. The detection of abnormal behavior could be a potential case of MCI illness.

In another aspect, a system for detection of Mild Cognitive Impairment (MCI) in a subject is provided. The system comprises a memory storing instructions and a centralized database, one or more communication interfaces; and one or more hardware processors coupled to the memory via the one or more communication interfaces, wherein the one or more hardware processors are configured by instructions to: receive sensor data from a plurality of sensors, wherein the received sensor data indicates Activities of Daily Living (ADL) pertaining to a subject for a specific time interval. Further, corrupt sensor data in the received sensor data is substituted, by using Long Short-Term Memory (LSTM), with correct sensor data to generate corrected sensor data, wherein the corrupt sensor data is substituted with the correct sensor data based on a learning pattern and historical data stored in a database. Further, a semantic vector representation of the corrected sensor data (long vector) is generated, wherein the semantic vector representation comprises a plurality of sub-vectors, wherein each of the plurality of sub-vectors comprise of a subset of the corrected sensor data of a pre-determined time interval. Furthermore, size of the semantic vector representation of the corrected sensor data is optimized, by using an auto encoder to generate an optimized vector data. Further to optimize, using an auto encoder, size of the semantic vector representation of the corrected sensor data to generate an optimized vector data comprises: applying a dimension reduction based window sizing technique on the semantic vector representation of the corrected sensor data. Then, a dynamic threshold parameter (ø) is estimated based on one or more similarity values obtained from a comparison of (i) the optimized vector data for the time interval with (ii) an adjacent optimized vector data comprising corresponding corrected sensor data stored in the database. Further, a comparison is performed for one or more similarities values with the dynamic threshold parameter. Upon detecting behavior deviation of the user, one or more hardware processors are further configured to analyze the semantic vector representation corresponding to the optimized vector data and performing a comparison of the analyzed semantic vector representation with a previous adjacent semantic vector representation by storing a start time and an end time specific to the behavior deviation of the user in a database. In an embodiment, one or more corresponding sub-vectors are analyzed based on the start time and the end time specific to the behavior deviation of the user and the analyzed one or more corresponding sub-vectors are tagged as one or more abnormal vectors. In an embodiment, one or more abnormalities indicative of behavior deviation of the subject are detected based on the comparison, wherein one or more random activities between the start time and the end time is compared and a flag indicative of an abnormal behavior is generated when duration of the one or more repeated random activities is less than or greater than an actual duration of a corresponding particular activity. The detection of abnormal behavior could be a potential case of MCI illness.

In yet another aspect, a non-transitory computer readable medium for detection of Mild Cognitive Impairment (MCI) in a subject is provided. The method includes receiving sensor data from a plurality of sensors, wherein the received sensor data indicates Activities of Daily Living (ADL) pertaining to a subject for a specific time interval. Further corrupt sensor data in the received sensor data is substituted, by using Long Short-Term Memory (LSTM), with correct sensor data to generate corrected sensor data, wherein the corrupt sensor data is substituted with the correct sensor data based on a learning pattern and historical data stored in a database. Further, a semantic vector representation of the corrected sensor data (long vector) is generated, wherein the semantic vector representation comprises a plurality of sub-vectors, wherein each of the plurality of sub-vectors comprise of a subset of the corrected sensor data of a pre-determined time interval. Furthermore, size of the semantic vector representation of the corrected sensor data is optimized, by using an auto encoder to generate an optimized vector data. Then, a dynamic threshold parameter ($\Theta$) is estimated based on one or more similarity values obtained from a comparison of (i) the optimized vector data for the time interval with (ii) an adjacent optimized vector data comprising corresponding corrected sensor data stored in the database. Further, a comparison is performed for one or more similarities values with the dynamic threshold parameter; upon detecting behavior deviation of the user, analyzing the semantic vector representation corresponding to the optimized vector data and performing a comparison of the analyzed semantic vector representation with a previous adjacent semantic vector representation; and storing a start time and an end time specific to the behavior deviation of the user in a database. Further one or more corresponding sub-vectors is analyzed based on the start time and the end time specific to the behavior deviation of the user; and tagging the analyzed one or more corresponding sub-vectors as one or more abnormal vectors. Finally one or more abnormalities indicative of behavior deviation of the subject is detected based on the comparison, wherein one or more random activities between the start time and the end time is compared and a flag indicative of an abnormal behavior is generated when duration of the one or more repeated random activities is less than or greater than an actual duration of a corresponding particular activity. The detection of abnormal behavior could be a potential case of MCI illness.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

Figure 1:
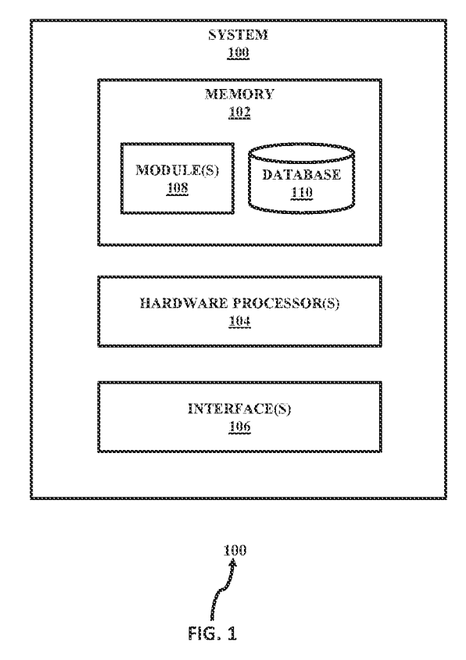
FIG. 1 illustrates an exemplary block diagram of a system for Mild Cognitive Impairment (MCI) detection in accordance with some embodiments of the present disclosure.

FIG. 1 illustrates an exemplary block diagram of a system 100 for Mild Cognitive Impairment (MCI) detection according to an embodiment of the present disclosure. The system 100 may also referred as a MCI detector hereinafter. In an embodiment, the system 100 includes one or more processors 104, communication interface device(s) or input/output (I/O) interface(s) 106, and one or more data storage devices or memory 102 operatively coupled to the one or more processors 104. The memory 102 comprises one or more modules 108 and the database 110. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical subject interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
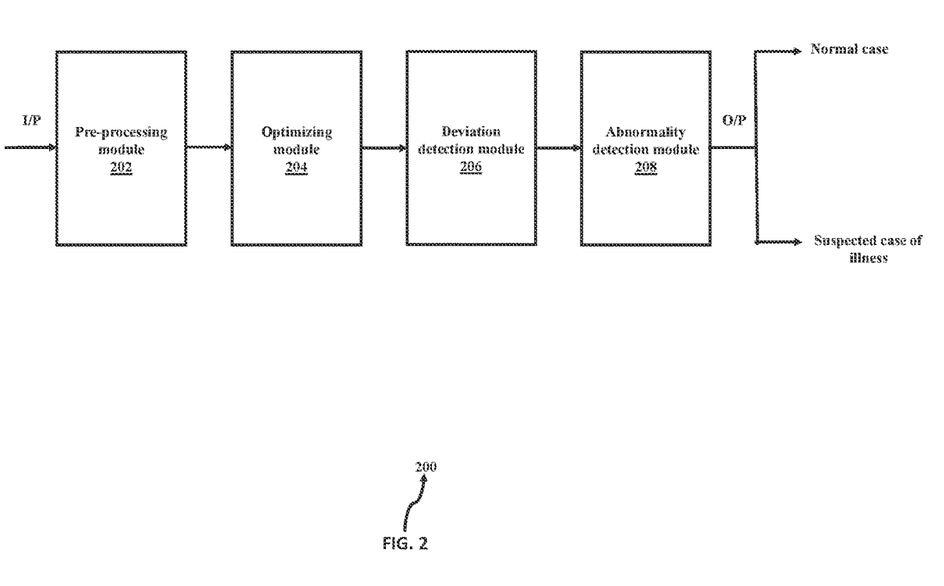
FIG. 2 is a functional block diagram of various modules stored in module(s) of a memory of the system of FIG. 1 in accordance with some embodiments of the present disclosure.

FIG. 2, with reference to FIG. 1, is a block diagram of various modules 108 stored in the memory 102 of the system 100 of FIG. 1 in accordance with an embodiment of the present disclosure. In an embodiment of the present disclosure, the module 108 comprises a pre-processing module 202, an optimizing module 204, a deviation detection module 206 and an abnormality detection module 208. In an embodiment of the present disclosure, the pre-processing module 202, the optimizing module 204, the deviation detection module 206 and the abnormality detection module 208 are implemented as at least one of a logically self-contained part of a software program, a self-contained hardware component, and/or, a self-contained hardware component with a logically self-contained part of a software program embedded into each of the hardware component that when executed perform the above method described herein.

Figure 3:
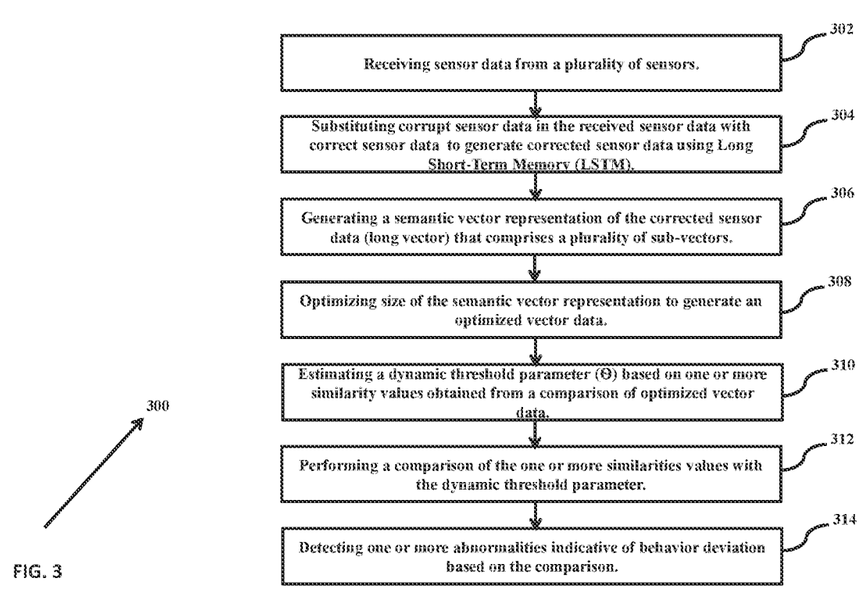
FIG. 3 is an exemplary flow diagram illustrating a method for MCI detection using the system of FIG. 1 in accordance with some embodiments of the present disclosure.

FIG. 3, with reference to FIGS. 1-2, is an exemplary flow diagram illustrating a method for MCI detection using the system 100 of FIG. 1 according to an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 and the modules 202-208 as depicted in FIGS. 1-2, and the flow diagram.

In an embodiment of the present disclosure, step 302, the pre-processing module 202 receives sensor data from a plurality of sensors, wherein the received sensor data indicates Activities of Daily Living (ADL) pertaining to a subject for a specific time interval from a smart environment. In an embodiment, a plurality of non-intrusive sensors are embedded in a smart environment such as an old age home, orphanage or home and so on. The plurality of sensors used are passive (such as photographic, thermal, electric field sensing, chemical, infrared and so on) and binary (such as pressure switches, temperature switches, thru-beam photoelectric sensors, proximity sensors, push buttons and so on) sensors which are unobtrusive and non-intrusive and which would hereafter be referred to as non-intrusive sensors. The plurality of non-intrusive sensors continuously monitor routine activities of subjects housed in the smart environment. The plurality of non-intrusive sensors are connected to a variety of network devices, including routers, bridges, servers, computing devices, storage devices. In an embodiment, sensor data comprises data such as sensor replication, sensor status, sensor position, remaining battery life (used to power up the sensor), current date and time. Further, the collected sensor data needs to be further analyzed in cumulating with other attributes stored to label ADL or routine activities. For example, sensor data collected is illustrated below in table 1:

TABLE 1

| Date | Time | Sensor status | Sensor replication | Location of sensor | Sensor type |
|---|---|---|---|---|---|
| 2017:12:01 | 00:00:37 | OK | 1 | door | PIR |
| 2017:12:01 | 00:00:37 | NOK | 0 | bed | Vibration |
| 2017:12:01 | 00:00:37 | OK | 23 | Bed room | temperature |
| 2017:12:01 | 00:00:37 | OK | 0 | kitchen | PIR |

As can be depicted from the above Table 1, sensor data indicates ADL pertaining to a subject for a specific time interval from a smart environment. If value of sensor status is set to 'OK' then it is monitoring routine activities (betokens it is getting powered up) else the sensor status is set to "NOK", which means that the routine activities are not being monitored. The routine activities may not be monitored due to various reasons such as battery drain, communication outage, malfunctioning and so on. Further, the 'Sensor Replication' parameter indicates number of instances of the sensor such as temperature or pressure sensors which are usually replicated. Further, the parameter 'Location of sensor' could give information about physical location of the sensor. The collected sensor data is labeled on basis of sensor replication, sensor status and sensor position" if on Jan. 1, 2017 at 1:00:07 sensor position is bed, sensor replication is 1 and sensor status is OK, then sensor labelling would be Jan. 1, 2017 at 1:00:07 subject is on the bed and activity is labeled as resting/sleeping.

In an embodiment of the present disclosure, at step 304, the sensor data received from a plurality of sensors is processed (by the hardware processors 104) to substitute corrupt sensor data with correct sensor data. The corrupt sensor data is substituted with correct sensor data to generate corrected sensor data (long vector) using Long Short-Term Memory (LSTM) techniques, based on a learning pattern and historical data stored in a database. Further, LSTM models known in art such as stateful LSTM are used to substitute corrupt data with correct data. In an embodiment, a stateful model may comprise several layers which are connected in numerous ways such as one fully connected input layer of dimension one, two hidden layers of dimension fifty, one fully connected output layer of dimension one and so on. Further the stateful LSTM may also comprise of Activation function such as Rectified Linear Unit (ReLU) and Minimization Parameter such as Root Mean Square Deviation (RMSE) and so on. Furthermore, the corrected sensor data is further processed to fill any gaps in sensor data. The gaps in the sensor data occurs due to sensor failure, that are captured by the "sensor status" parameter during the sensor data collection process, wherein "sensor status" parameter is set to "NOK" in case of sensor failure as shown in Table 1. Further, the sensor gaps are filled up using Recurrent Neural Network (RNN) based techniques known in art, wherein RNN predicts the next state of the system on the basis of precedent two states of the system. Hence, the RNN technique proposes to uses precedent two states to predict next day data, wherein total number of sensor data with data gaps (M), predicted sensor data ($V_{predicted}$) and actual sensor data ($V_{actual}$) and could be expressed as shown below;

$$\text{Accuracy} = \frac{\Sigma_1^M 100 - (V_{predicted} - V_{actual})}{M}$$

In an embodiment, a comparison of accuracy of estimation of a few known techniques along with RNN is shown in table 2 below:

TABLE 2

| Techniques | Accuracy |
|---|---|
| Using HMM model | 79 |
| Using average of last one week | 85 |
| Using average of last one month average of the same day | 89.5 |
| Using RNN | 92 |

Figure 4:
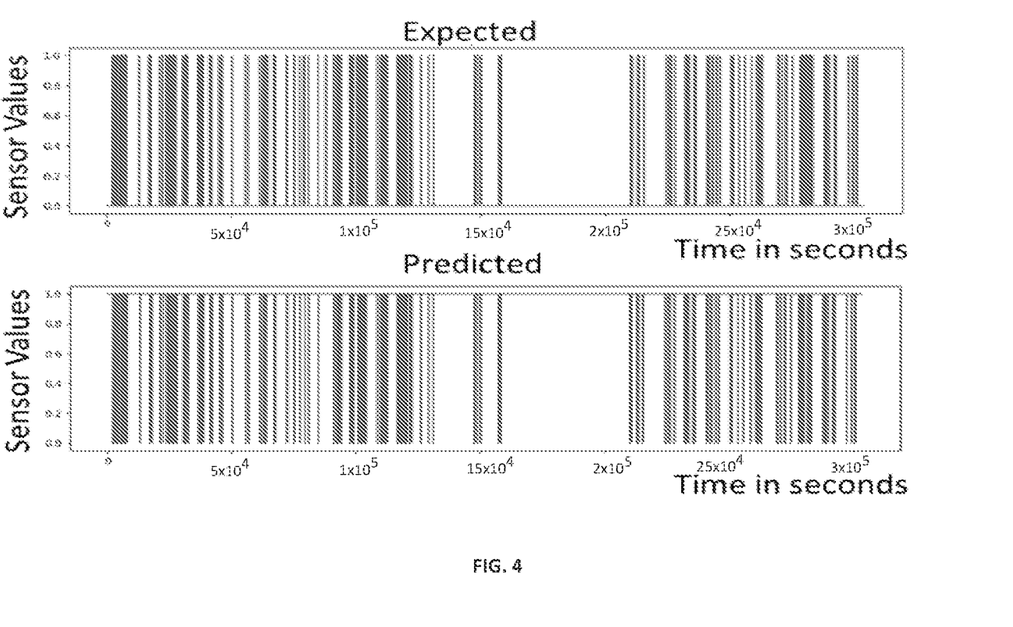
FIG. 4 illustrates predicted and expected graphs of sensor value using RNN techniques, according to some embodiments of the present disclosure.

It is evident from the Table 2 that the prediction accuracy technique of RNN is better compared to other existing technologies. In an embodiment, predicted along with expected graphs using RNN is as shown in FIG. 4.

In an embodiment of the present disclosure, at step 306, a semantic vector representation of the corrected sensor data (long vector) is generated by the hardware processors 104, wherein the semantic vector representation comprises a plurality of sub-vectors, wherein each of the plurality of sub-vectors comprise of a subset of the corrected sensor data of a pre-determined time interval. In an embodiment, vector and sub-vectors could be represented as long vector and short vector, wherein long vector comprises of multiple short vector. Further, in an example embodiment, long vector represents 24 hours data of a subject, while short vectors represent activity of a subject for a pre-defined time interval (e.g., say each short vector may represent data of 1 second). The long and short vectors may be expressed using parameters sensor replication (s), number of sensors (n) & time stamp (t) as shown below;

$$(V_n^i = (t_1; s_1; s_2; \ldots ; s_n); (t_2; s_1; s_2; \ldots ; s_n); \ldots ; (t_{86400}; s_1; s_2; \ldots ; s_n);$$

Where,
($V_x^i$) is $x^{th}$ long vector for $i^{th}$ subject
($t_j$; $S_1$; $S_2$; $\ldots$ : $S_N$) is a single short vector at the $j^{th}$ second of a day.

Figure 5:
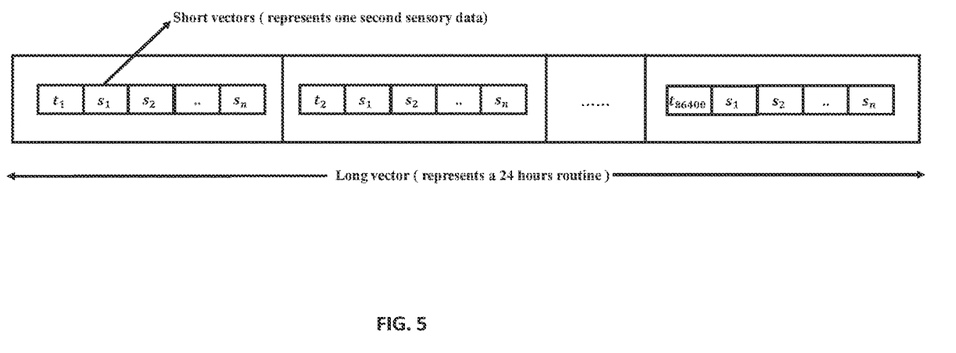
FIG. 5 illustrates vector and sub-vectors represented as a long vector and short vector(s) for a day respectively, in accordance with some embodiments of the present disclosure.

In an embodiment, representation of long and short vectors for a day (24 hours) using parameters s, n, t shown in FIG. 5.

In an embodiment of the present disclosure, at step 308, the hardware processors 104 optimize size of the semantic vector representation of the corrected sensor data using the optimizing module 204 to generate an optimized vector data. The dimensions of corrected sensor data (long vectors) is (very) high for manual interpretation as it comprises of Activities of Daily Living (ADL) of a human being, wherein, in an embodiment, a long vector represents a daily routine (24 hours) of a person which further comprises of 86400 short vectors. Further, since sensor data is received from a plurality of sensors (N), the received sensor data comprises 84600 short vectors which could be represented as 84600*(N+1). Hence the high dimensional corrected sensor data is optimized in the optimizing module 204. In an embodiment, the optimizing module 204 comprises an autoencoder, which is a neural network based model to reduce dimensions of the high dimensional corrected sensor data. The autoencoder reduces size of semantic vector representation of the corrected sensor data by applying dimension reduction based window sizing technique (e.g., known in the art technique), on the semantic vector representation of the corrected sensor data to generate the optimized vector data.

In an embodiment of the present disclosure, at step 310, the hardware processor 104 utilizes the deviation detection module for estimating a dynamic threshold parameter (ø) based on one or more similarity values obtained from a comparison of (i) the optimized vector data for the time interval with (ii) an adjacent optimized vector data comprising corresponding corrected sensor data stored in the database 110. In an embodiment, the step of estimating a dynamic threshold parameter (ø) is preceded by comparing (i) the optimized vector data for the time interval with (ii) an adjacent optimized vector data comprising corresponding corrected sensor data stored in the database 110. The dynamic threshold parameter (ø) is personalized for each subject. The initial value of the (ø) is set to the measure of the extent of the similarity between the first two long vectors. The extent of similarity is measured on the basis of normalized (on a scale of 0-10) value of the difference of two adjacent long vectors. In an embodiment, extent of similarity based of normalized (on a scale of 0-10) value of the difference of two adjacent long vectors could be 8.5, 9.0 and 9.5 from which 9.5 was chosen as initial value of (ø). Further, for next comparison threshold range is set to (2-ø$_{previous}$+2). Further the current extent of similarity is stored as ø$_{current}$ and accordingly ø$_{previous}$ is updated as ø$_{previous}$α*ø$_{current}$-ø$_{previous}$). The values of ø$_{current}$ and ø$_{previous}$ are further used to detect behavior deviation. Below, table 3, is an illustrative example of comparison of the one or more similarities values such as $ø_{current}$ and $ø_{previous}$ in accordance with some embodiments of the present disclosure:

TABLE 3

| Subject | $Ø_{current}$ | $Ø_{previous}$ | Behavior deviation |
|---|---|---|---|
| S003 | 0.7520888203 | 0.7389274366 | 1 |
| S006 | 0.229625989 | 0.2456352491 | 0.1 |
| S008 | 0.6351863625 | 0.583631748 | 0.3 |
| S010 | 0.4076552818 | 0.3841365171 | 0.3 |
| S013 | 1 | 1 | 0.1 |

As can be depicted from the above Table 3, the table contains dynamic threshold parameter ((ø)) personalized for respective subjects taken under a specific time.

In an embodiment of the present disclosure, at step 312, the hardware processor 104 performs a comparison of the one or more similarities values with the dynamic threshold parameter (ø) in deviation detection module 206. During the comparison $ø_{current}$ and $ø_{previous}$ if the difference is greater than 1 then deviation is detected in the behavior of a subject, but changes are not reflected in the value of $ø_{previous}$. However, α is set equal to 0.01 to ensure the slow evolution of ϴ with time to ensure it can detect diversions. Hence when the similarity between two adjacent vectors is less than a particular threshold (ø, then deviation is detected as shown in Table 2 and the vectors are shared with the abnormality detection module 208 for further analysis.

Figure 6:
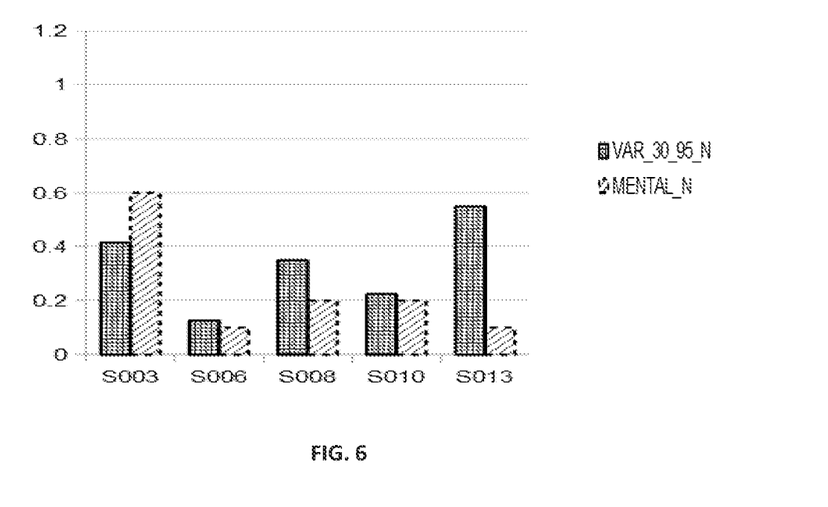
FIG. 6 illustrates a graph representing abnormalities indicative of behavior deviation of a subject, in accordance with some embodiments of the present disclosure.

In an embodiment of the present disclosure, at step 314, the hardware processors 104 detect one or more abnormalities indicative of behavior deviation of the subject by using the abnormality detection module 208, based on the comparison of one or more similarities values with the dynamic threshold parameter (ø). Upon detection of behavior deviation, the semantic vector representation corresponding to the optimized vector data is analyzed to perform a comparison of the analyzed semantic vector representation with a previous adjacent semantic vector representation, while storing a start time and an end time specific to the behavior deviation of the subject in a database. In an embodiment of the present disclosure, the corresponding sub-vectors are analyzed based on the start time and the end time specific to the behavior deviation of the subject and the analyzed one or more corresponding sub-vectors are tagged as one or more abnormal vectors. Further, the detected abnormal sub-vectors are analyzed to detect one or more random activities between the start time and the end time, and a flag indicative of an abnormal behavior is generated when duration of the one or more repeated random activities is less than or greater than an actual duration of a corresponding particular activity. FIG. 6 illustrates detection of abnormalities indicative of behavior deviation of a subject, in accordance with some embodiments of the present disclosure.

In an embodiment of the present disclosure, the one or more hardware processors 104 are further configured by the instructions to perform Principal Component Analysis (PCA) on the behavior deviation of the subject detected for the specific time interval to obtain a set of eigen vectors based on a variance for the behavior deviation, and compute a personal variation index based on the set of eigen vectors. In an embodiment of the present disclosure, the one or more hardware processors 104 are further configured by the instructions to flag behavior of the subject is flagged as an abnormal behavior based on comparison of personal variation index with a pre-defined threshold. The flagging techniques may be known in art such as color code or rank based flagging. Further, in color code flagging technique, red color may indicate MCI detection, amber may indicate a potential case while green may be a normal case, without MCI detected.

In an embodiment, personal variation index is computed in several steps, wherein the behavior of semantic vector representation (BS) of the corrected sensor data (long vector) is computed first. In an embodiment, the semantic vector representation of the corrected sensor data (long vector), taken at 1 Hz sampling is BS which is array of length 24*60*60, wherein value at first position is 1 if sensor output at that time is 1. The behavior of each sensor $BS_{sensor}$ is obtained using a configuration parameter, wherein each day is segmented into fragments of $T_f$(20-30) minutes. Hence the $i^{th}$ entry for each sensor at time duration $T_f$ would be expressed as follows;

$$BS_{sensor} = i*T_f \text{ to } (i+1)T_f \text{ minutes}$$

Considering an example of i=20 for $T_f$=20, wherein $20^{th}$ entry in array corresponds to (400-420) minutes, which excluding the time instance 420 minutes. Further, if $i^{th}$ entry $BS_{sensor}(i)$ is 1 then at least one entry in $BS_{sensor}$ is 1, else $BS_{sensor}(i)$ is 0.

The $BS_{sensor}$ of the plurality of sensors is used to estimate Overall Behavior OB for any time instance, which is expressed as follows;

$$OB = [BS_{sensor_1} BS_{sensor_2} BS_{sensor_3} \ldots, BS_{sensor_N}]$$

The computed OB is further used to compute $OB_{Average}$ or N days, which is expressed as follows;

$$OB_{Average} = \text{mean}(OB_{N-Day})$$

Further, behavior deviation is computed for each day, which is expressed as follows;

$$BD_{day} = OB_{N-Day} - OB_{Average}$$

Furthermore, Principal Component Analysis, known in art, is performed on $BD_{Day}$, wherein $BD_{Day}$ comprises collection of N vectors. Further, eigenvectors (m) necessary for 90% variance for BD is estimated, which is further used to compute personalVariationIndex for time interval N, which is expressed as:

$$\text{personalVariationIndex}_{TimeInterval} = m/N$$

Below in table 4, is an illustrative example of computation of personalVariationIndex in accordance with some embodiments of the present disclosure:

TABLE 4

| Subject | Behavior analysis |
|---|---|
| Duration | 1 |
| rankOfMat | 89 |
| $ϴ_{80}$ | 60 |
| $ϴ_{90}$ | 73 |
| $ϴ_{95}$ | 80 |
| Days/Time | 90 |
| personalVariationIndex | 0.811111 |

As can be depicted from the above Table 4, table 4 contains personalized computation of persoanlVariationIndex for a subject taken under a specific time.

In an embodiment, considering N as 30, sliding window method, known in art is performed to obtain personalVariationIndex for 30, wherein the time series can vary as 1-30, 5-35 and so on. Furthermore, the computed personal variation index is compared with a pre-defined threshold (0.85) to flag of a behavior of the subject as an abnormal behavior. Further in case personal Variation Index is closer to 0.085 such as 0.7, then personal Variation Index and flags are estimated for different time frames. In an embodiment, if the estimated flags are raised for 2-4 consecutive periods, then an alarm is raised for abnormality and MCI detection. In an embodiment, if personalVariationIndex is above 0.7 and below 0.85 it is monitored further using 60 minutes and 20 minutes duration to compute values of $i_1$=personal VariationIndex$_{60}$ and $i_2$32 personalVariationIndex$_{20}$ and flag is raised if ($i_1$>0.8, i2>0.8) or if ($i_1$>0.9) or if ($i_1$>0.7, i2>0.95). If flag is raised at frequent intervals (that is 1 in 3-5 consecutive trials for 25 day overlap), the personalVariationIndex is re-compute with N as 40 day and 30 day overlap (i.e. N=40) and continuously monitored for consecutive flagging to confirm abnormality or detect MCI as illustrated in FIG. 6 with a graph representing detection of abnormal behavior based on comparison of personal variation index with a pre-defined threshold, in accordance with some embodiments of the present disclosure, wherein the x-axis represents subjects, while y-axis represents behavioral deviation.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Hence the proposed system and method provides a continuous monitoring platform for early detection of Mild Cognitive Impairment (MCI). The embodiment, provides a method for detection of Mild Cognitive Impairment (MCI) by continuous monitoring routine activities of subjects, housed in a smart environment by plurality of non-intrusive sensors. Further the collected sensor data is pre-processed in several stages, which includes pre-processing of sensor data, behavior deviation detection, abnormality detection and so on to detect if a could be a potential case of MCI illness.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for detection of Mild Cognitive Impairment(MCI) in a subject, comprising:
   receiving sensor data from a plurality of sensors, wherein the received sensor data indicates Activities of Daily Living (ADL) pertaining to a subject for a specific time interval (302);
   substituting, by using Long Short-Term Memory (LSTM), corrupt sensor data in the received sensor data with correct sensor data to generate corrected sensor data, wherein the corrupt sensor data is substituted with the correct sensor data based on a learning pattern and historical data stored in a database (304);
   generating a semantic vector representation of the corrected sensor data, wherein the semantic vector representation comprises a plurality of sub-vectors, wherein each of the plurality of sub-vectors comprise of a subset of the corrected sensor data of a pre-determined time interval (306);

optimizing, by using an auto encoder, size of the semantic vector representation of the corrected sensor data to generate an optimized vector data (308);

estimating a dynamic threshold parameter (ø) based on one or more similarity values obtained from a comparison of (i) the optimized vector data for the time interval with (ii) an adjacent optimized vector data comprising corresponding corrected sensor data stored in a database (310);

performing a comparison of the one or more similarities values with the dynamic threshold parameter (312); and detecting, based on the comparison, one or more abnormalities indicative of behavior deviation of the subject (314).

2. The processor implemented method of claim 1, wherein the step of optimizing, by using an auto encoder, size of the semantic vector representation of the corrected sensor data to generate an optimized vector data comprises: applying a dimension reduction based window sizing technique on the semantic vector representation of the corrected sensor data.

3. The processor implemented method of claim 1, further comprising upon detecting behavior deviation of the subject, analyzing the semantic vector representation corresponding to the optimized vector data and performing a comparison of the analyzed semantic vector representation with a previous adjacent semantic vector representation; and storing a start time and an end time specific to the behavior deviation of the subject in the database.

4. The processor implemented method of claim 3, further comprising analyzing one or more corresponding sub-vectors based on the start time and the end time specific to the behavior deviation of the subject; and tagging the analyzed one or more corresponding sub-vectors as one or more abnormal vectors.

5. The processor implemented method of claim 4, further comprising detecting one or more random activities between the start time and the end time; and generating a flag indicative of an abnormal behavior when duration of the one or more repeated random activities is less than or greater than an actual duration of a corresponding particular activity.

6. The processor implemented method of claim 1, further comprising performing a Principal Component Analysis (PCA) on the behavior deviation of the subject detected for the specific time interval to obtain a set of eigen vectors based on a variance for the behavior deviation; and computing a personal variation index based on the set of eigen vectors.

7. The processor implemented method of claim 6, further comprising performing a comparison of the personal variation index with a pre-defined threshold; and flagging behavior of the subject as an abnormal behavior based on the comparison.

8. A system (100), comprising:
a memory storing instructions(102) and a centralized database (110);
one or more communication interfaces(106); and
one or more hardware processors(104) coupled to the memory via the one or more communication interfaces, wherein the one or more hardware processors are configured by instructions to:

receive sensor data from a plurality of sensors, wherein the received sensor data indicates Activities of Daily Living (ADL) pertaining to a subject for a specific time interval;

substitute, by using Long Short-Term Memory (LSTM), corrupt sensor data in the received sensor data with correct sensor data to generate corrected sensor data in pre-processing module 202, wherein the corrupt sensor data is substituted with the correct sensor data based on a learning pattern and historical data stored in a database;

generate a semantic vector representation of the corrected sensor data, wherein the semantic vector representation comprises a plurality of sub-vectors, wherein each of the plurality of sub-vectors comprise of a subset of the corrected sensor data of a pre-determined time interval;

optimize, size of the semantic vector representation of the corrected sensor data to generate an optimized vector data;

estimate a dynamic threshold parameter (ø) based on one or more similarity values obtained from a comparison of (i) the optimized vector data for the time interval with (ii) an adjacent optimized vector data comprising corresponding corrected sensor data stored in the database in optimizing module 204;

perform a comparison of the one or more similarities values with the dynamic threshold parameter;

detect, based on the comparison, one or more abnormalities indicative of behavior deviation of the subject; and detect one or more abnormalities in the deviated compressed vector data by comparing the deviated compressed vector data with one or more reference vectors.

9. The system of claim 8, wherein the step to optimize the size of the semantic vector representation of the corrected sensor data is optimized to generate the optimized vector data by applying a dimension reduction based window sizing technique on the semantic vector representation of the corrected sensor data.

10. The system of claim 8, wherein the one or more hardware processors are further configured to, analyze, upon detecting behavior deviation of the subject, the semantic vector representation corresponding to the optimized vector data and perform a comparison of the analyzed semantic vector representation with a previous adjacent semantic vector representation, and store a start time and an end time specific to the behavior deviation of the subject in the database.

11. The system of claim 10, wherein the one or more hardware processors are further configured to analyze one or more corresponding sub-vectors based on the start time and the end time specific to the behavior deviation of the subject; and tag the analyzed one or more corresponding sub-vectors as one or more abnormal vectors performed.

12. The system of claim 11, wherein the one or more hardware processors are further configured to detect one or more random activities between the start time and the end time; and generate a flag indicative of an abnormal behavior when duration of the one or more repeated random activities is less than or greater than an actual duration of a corresponding particular activity.

13. The system of claim 8, wherein the one or more hardware processors are further configured to perform a Principal Component Analysis (PCA) on the behavior deviation of the subject detected for the specific time interval to obtain a set of eigen vectors based on a variance for the behavior deviation; and compute a personal variation index based on the set of eigen vectors.

14. The system of claim 13, wherein the one or more hardware processors are further configured to perform a comparison of the personal variation index with a pre-defined threshold; and flag behavior of the subject as an abnormal behavior based on the comparison.

15. The non-transitory computer-readable medium having embodied thereon a computer program for detection of Mild Cognitive Impairment (MCI) in a subject, the method comprising:

receiving sensor data from a plurality of sensors, wherein the received sensor data indicates Activities of Daily Living (ADL) pertaining to a subject for a specific time interval (302);

substituting, by using Long Short-Term Memory (LSTM), corrupt sensor data in the received sensor data with correct sensor data to generate corrected sensor data, wherein the corrupt sensor data is substituted with the correct sensor data based on a learning pattern and historical data stored in a database (304);

generating a semantic vector representation of the corrected sensor data, wherein the semantic vector representation comprises a plurality of sub-vectors, wherein each of the plurality of sub-vectors comprise of a subset of the corrected sensor data of a pre-determined time interval (306);

optimizing, by using an auto encoder, size of the semantic vector representation of the corrected sensor data to generate an optimized vector data (308);

estimating a dynamic threshold parameter ($\emptyset$) based on one or more similarity values obtained from a comparison of (i) the optimized vector data for the time interval with (ii) an adjacent optimized vector data comprising corresponding corrected sensor data stored in a database (310);

performing a comparison of the one or more similarities values with the dynamic threshold parameter (312); and detecting, based on the comparison, one or more abnormalities indicative of behavior deviation of the subject (314).

\* \* \* \* \*